United States Patent [19]
Balhoff et al.

[11] Patent Number: 5,789,631
[45] Date of Patent: Aug. 4, 1998

[54] PRODUCTION OF PERHALOBENZENES

[75] Inventors: John F. Balhoff; Ronny W. Lin, both of Baton Rouge, La.

[73] Assignee: Albemarle Corporation, Richmond, Va.

[21] Appl. No.: 756,104

[22] Filed: Nov. 25, 1996

[51] Int. Cl.[6] .......................... C07C 25/13; C07C 22/00
[52] U.S. Cl. .................................. 570/147; 570/206
[58] Field of Search ............................. 570/206, 147

[56] References Cited

U.S. PATENT DOCUMENTS

| | | | |
|---|---|---|---|
| 3,064,058 | 11/1962 | Duesel et al. | 260/646 |
| 3,240,824 | 3/1966 | Boudakian et al. | 260/646 |
| 3,277,192 | 10/1966 | Fielding et al. | 260/650 |
| 3,280,124 | 10/1966 | Boudakian et al. | 260/251 |
| 3,296,269 | 1/1967 | Boudakian et al. | 260/290 |
| 3,300,537 | 1/1967 | Bennett et al. | 260/649 |
| 3,303,197 | 2/1967 | Hazeldine et al. | 260/290 |
| 3,312,746 | 4/1967 | Fielding | 260/650 |
| 3,314,955 | 4/1967 | Boudakian et al. | 260/251 |
| 3,388,174 | 6/1968 | Fielding et al. | 260/650 |
| 3,408,412 | 10/1968 | Blackley et al. | 260/650 |
| 3,453,337 | 7/1969 | Bennett et al. | 260/650 |
| 3,485,839 | 12/1969 | Fuller | 260/251 |
| 3,574,775 | 4/1971 | Fuller | 260/650 |
| 3,852,365 | 12/1974 | Maher | 260/650 F |
| 3,965,197 | 6/1976 | Stepniczka | 570/147 |
| 4,069,262 | 1/1978 | Kunz | 260/646 |
| 4,174,349 | 11/1979 | Evans et al. | 260/544 F |
| 4,209,457 | 6/1980 | Fuller | 260/465 G |
| 4,226,811 | 10/1980 | Oeser et al. | 568/937 |
| 4,229,365 | 10/1980 | Oeser et al. | 260/465 G |
| 4,684,734 | 8/1987 | Kaieda et al. | 546/345 |
| 4,978,769 | 12/1990 | Kysela et al. | 570/147 |

FOREIGN PATENT DOCUMENTS

| | | | |
|---|---|---|---|
| 285453 | 8/1965 | Australia | 570/147 |
| 0678864 | 4/1994 | U.S.S.R. | |
| 0755668 | 8/1956 | United Kingdom . | |
| 0866810 | 5/1961 | United Kingdom . | |
| 0970746 | 9/1964 | United Kingdom . | |
| 0996498 | 6/1965 | United Kingdom . | |
| 1026290 | 4/1966 | United Kingdom . | |
| 1071323 | 6/1967 | United Kingdom . | |
| 1256082 | 12/1971 | United Kingdom . | |
| 1340421 | 12/1973 | United Kingdom . | |
| 1360327 | 7/1974 | United Kingdom . | |

OTHER PUBLICATIONS

Aromatic Fluoro Derivates. VIII. Reaction of chloronitro compounds with fluorides of alkali metals; Chemical Abstract; pp. 9706 and 9707 (1962).

"Interaction of Chloroaromatic with Alkali Metal Fluorides in the Presence of Crown–Ethers", Yakobson, et al., Journal of Flourine Chemistry; vol. 28(1985), pp. 73–87.

Heterocyclic Polyfluoro–compounds. Part VI. Preparation of Pentafluoropyridine and Chlorofluoropyridines from Pentachloropydine; By: R E. Banks, et al; J. Chem. Soc., (1965) pp. 594–597.

"Preparation of Polyfluoroaromatic Compounds by the Reaction of Perhalogeno–aromatic Compounds with Potassium Fluoride in Sulpholan"; By: G. Fuller; Journal Chemical Society, (1965); pp. 6264–6267.

Solvent–free Fluorination of Partially–Chlorinated Heterocyclics: Synthesis of 2,6–Difluoropyridie from 2,6 Dichloropyridine; By: Boudakian, et al., J. Hetercyclic Chem. (1968); pp. 683–684.

"Aromatic Nucleophilic Substitution Reactions", Chem. Reviews; American Chemical Society; vol. 48(1951); pp. 273–277 and p. 405.

"Polyfluoro–heterocyclic Compounds. Part I. The Preparation of Fluoro–, Chlofluoro–, and Chlorofluorohydro–pyridines"; By: R. D. Chambers, et al; J. Chemical Society (1964); pp. 3573–3576.

"Aromatic Fluorine Compounds. XI. Replacement of Chlorine by Fluorine in Halopyridines"; By: G. C. Finger, et al; Journal of Org. Chemical (1963); vol. 28, pp. 1666–1668.

"Aromatic Fluorine Compounds. VIII. Plant Growth Regulators and Intermediates"; By: G. C. Finger, et al; Journal of American Chemical Society (1959); vol. 81, pp. 94–101.

"Dimethyl Sulphone as a Reaction Solvent for the Preparation of Aromatic Fluorides"; By: L. D. Starr; Chemistry and Industry (1962); pp. 1328–1329.

"Preparation de derives perhalogenes aromatiques polyfluores par reaction d'echange d'halogene, utilisant une phase sel fondu"; By: J. Hitzke; Bulletin de la Societe Chimique De Franc (1974); No. 5–6; pp. 811–814.

"LaFluoration De L'Hexachlorobenzene Et De LA Pentachloropyridine En Milieu De Potassium Solide"; By: J. Hitzke; Journal of Fluorine Chemistry (1980); vol. 16, pp. 103–128.

"Halex Fluorination of 1,2,4,5–tetrachlorobenzene in a pressure reactor"; By: Yoshikazu Kimura (1992); Journal of Fluorine Chemistry, vol. 59, pp. 289–291.

Tetraphenylphosphonium bromide–catalyzed 'Halex'fluorination of chloroaryl sulfonyl chlorides; By: Yoshikazu Kimura; Journal of Fluorine Chemistry, (1991); vol. 55, pp. 335–337.

"Halex Fluorination of Chlorinated Benzaldehydes and Benzoyl Chlorides"; By: R. Eric Banks; Journal of Fluorine Chemistry (1990); vol. 46, pp. 529–537.

(List continued on next page.)

*Primary Examiner*—Alan Siegel
*Attorney, Agent, or Firm*—Philip M. Pippenger

[57] ABSTRACT

An anhydrous mixture containing a liquid phase and a solids phase formed from components comprising finely-divided sodium fluoride, hexabromobenzene, and a phosphonium catalyst, and optionally a liquid aprotic solvent/diluent, is heated at a temperature and for a time at which sodium bromide and at least one hexahalobenzene containing at least two fluorine atoms are produced. Preferably, the sodium fluoride is activated by one or more of procedures specified herein.

15 Claims, No Drawings

OTHER PUBLICATIONS

La Fluoration par kf de Perhalogenes Organiques Aromatiques en Presence de Faibles Quantites de Sulfolane ou D'Eau. Spectres de Masses des Melanges Obtenus en Serie Benzenique; By: J. Hitxke; Journal of Flourine Chemistry (1981); vol. 18, pp. 101–115.

Aromatic Fluorine Compounds. VII. Replacement of Aromatic –Cl and –NO 2 Groups by –F 1,2; By: G. C. Finger (1956); Contributed from the Illinois State Geological Survey; vol. 78, pp. 6034–6036.

"The Replacement of Chlorine by Fluorine in Organic Compounds"; By: Hans Gottlieb; Journal American Chemical Society (1936); vol. 58, pp. 532–533.

Preparation of 3–Fluorophthalic Anhydride; By: Adam Heller; J. Org. Chem. (1960); vol. 25, pp. 834–835.

"Fluorination of Perhalobenzenes with Potassium Fluoride in Polar Solvents"; By: G. W. Holbrook, et al; J. Org. Chem. (1966), vol. 31, pp. 1259–1261.

The Synthesis of Highly Fluorinated Compounds by Use of Potassium Fluoride in Polar Solvents; By: John T. Naynard; J. Org. Chem. (1963); vol. 28, pp. 112–115.

The Synthesis of Pentafluorobenzoic Acid and a New Prification of Chloropentafluorobenzene; By: D. E. Pearson; Georg Thieme Publishers (1978); p. 127.

The Chemistry of 'Naked'Anions. I Reactions of the 18–Crown–6 Complex of Potassium Fluoride with Organic Sustrates in Aprotic Organic Solvents1; Journal of the Amiercan Chemical Soc.; (1974) pp. 2250–2252.

"The Cyclohexylation of Touluene and Ethylbenene using Ethylaluminium Halides"; By: I. V. Nicolescu, et al; Chemistry and Industry (1962), p. 1329.

Polyfluoroarenes. Part XVI. A Convenient Synthesis of Pentafluorobenzonitrile; By: J. M. Birchall; Journal Chemistry Society (1971); pp. 1341–1342.

Lundin, et al., "Investigation of Methods of Preparing Polyfluoroaromatic Compounds", Trudy Instituta Khimii, vol. 16, 1968, pp. 67–73.

Vorozhtsov, et al., "Formation of Chloroheptafluorotoluenes in the Reaction of Hexachlorobenzene With Potassium Flouride", Zhurnal Vsesoyuznoe Khimicheskoe Obschestvo im. D.I. Medeleeva, vol. 14,(1), 1969, p. 114.

PRODUCTION OF PERHALOBENZENES

REFERENCE TO OTHER APPLICATIONS

Reference is invited to the following copending applications now commonly owned by the same assignee as the present application: U.S. applications Ser. No. 08/754,338 filed Nov. 22, 1996; and Ser. Nos. 08/756,107 filed Nov. 25, 1996, 08/756,103 filed Nov. 25, 1996, and 08/756,105, each filed Nov. 25, 1996.

TECHNICAL FIELD

This invention relates to the synthesis of perhalobenzenes having in the molecule at least two fluorine atoms with the balance, if any, being bromine atoms.

BACKGROUND

Halogen exchange reactions for producing perhalobenzenes containing at least two fluorine atoms per molecule have been extensively studied heretofore. Typically they involve the reaction of hexachlorobenzene with potassium fluoride, rubidium fluoride or cesium fluoride by heating the reactants to extremely high temperatures (above about 400° C.) in the absence of an ancillary diluent or solvent, or by conducting the reaction at temperatures of around 200°–230° C. in an aprotic solvent such as sulfolane. In either case, the use in this reaction of sodium fluoride is not practical as the yields of polyfluorochlorobenzenes are minimal. For example, it is reported in Brit. 996,498 that in sulfolane at 230°–240° C. "sodium fluoride shows little reactivity as a fluorinating agent; most of the hexachlorobenzene is recovered, but traces of a material believed to be pentachlorofluorobenzene are produced."

It would be extremely desirable and economically advantageous if a way could be found to form perhalobenzenes having two or more fluorine atoms per molecule by a halogen exchange reaction using sodium fluoride as the fluorine source.

This invention is deemed to achieve this beneficial objective in an efficient, practical manner.

THE INVENTION

Pursuant to this invention use is made of hexabromobenzene as the initial perhalobenzene reactant. And in addition, the reaction with sodium fluoride is conducted in the liquid phase using a phosphonium catalyst. There are two general ways by which the liquid phase reaction can be conducted. In one case the reaction is performed at a temperature above the melting point of hexabromobenzene (about 306° C.), using a sufficient quantity of hexabromobenzene to provide a liquid phase at this temperature. In this case no ancillary solvent or diluent is used. In the other case the reaction is performed in an ancillary solvent or diluent, namely an anhydrous or essentially anhydrous aprotic solvent that remains in the liquid state of aggregation under the selected reaction temperature(s) and pressure(s).

Thus this invention provides a process which comprises heating an anhydrous mixture containing a liquid phase and a solids phase formed from components comprising finely-divided sodium fluoride, hexabromobenzene, and a phosphonium catalyst, and optionally a liquid aprotic solvent/diluent, at a temperature and for a time at which sodium bromide and at least one hexahalobenzene containing at least two fluorine atoms are produced. The principal fluorinated products formed in the process can be represented by the formula, $C_6F_nBr_{n-6}$, where n is in the range of from 2 to 6 inclusive, and preferably in the range of 3 to 5 inclusive. The coproduct, sodium bromide, can be recovered from the solids that remain in the reaction mixture after removal from the reaction zone. In addition, the recovered sodium bromide can be processed to produce bromine which can be used, for example, in producing hexabromobenzene. Thus this invention makes it possible to reutilize bromine in a recycling system involving hexabromobenzene to sodium bromide to bromine to hexabromobenzene, and so on.

Another embodiment is a process which comprises (a) brominating benzene with bromine in the presence of a Lewis acid catalyst to form hexabromobenzene; (b) forming an anhydrous mixture containing a liquid phase and a solids phase from components comprising at least a portion of said hexabromobenzene, finely-divided sodium fluoride, and a phosphonium catalyst, and optionally a liquid aprotic solvent/diluent; and (c) heating said mixture at a temperature and for a time at which sodium bromide and at least one hexahalobenzene containing at least two fluorine atoms are produced. In this process, liquid bromine from step (a) can be included in the mixture formed in (b) and heated in (c). Suitable Lewis acid catalysts include aluminum chloride, ferric chloride, zinc chloride, and analogous compounds. The bromination reaction to produce hexabromobenzene is conducted at suitable temperatures within the range of about 10° and about 70° C.

In another embodiment, one or more hexahalobenzenes containing one to four fluorine atoms (more preferably three to four fluorine atoms) with the balance being bromine atoms, is included in the reaction mixture. These hexahalobenzenes can be recovered from one or more prior batch operations conducted pursuant to this invention, or they can be directly recycled, continuously or intermittently, during the course of process of this invention conducted on a continuous basis.

The phosphonium catalysts used in the process are of two general types. For reactions conducted in the presence of one or more aprotic solvents or diluents, the catalyst as charged to the reaction mixture is a tetra(dihydrocarbylamino)phosphonium halide. Such compounds can be represented by the formula:

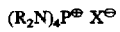

$(R_2N)_4P^{\oplus} X^{\ominus}$ where each R is, independently, a hydrocarbyl group, preferably an alkyl group, and X is a halogen atom, preferably a fluorine or bromine atoms, and most preferably a bromine atom. Examples of such phosphonium compounds are:

tetrakis(diethylamino)phosphonium fluoride
tetrakis(dibutylamino)phosphonium bromide
tris(diethylamino)(dipropylamino)phosphonium iodide
tetrakis(dibutylamino)phosphonium iodide
tris(dibutylamino)(diethylamino)phosphonium iodide
tris(dipropylamino)(diheptylamino)phosphonium iodide
tetrakis(dipropylamino)phosphonium bromide
tris(diethylamino)(dihexylamino)phosphonium iodide
tris(diethylamino)(dibutylamino)phosphonium iodide
tris(dipropylamino)(heptylpropylamino)phosphonium iodide
tetrakis(dipropylamino)phosphonium iodide
tris(dipropylamino)(ethylpropylamino)phosphonium iodide
tetrakis(diethylamino)phosphonium iodide
tetrakis(diethylamino)phosphonium bromide
tetrakis(diphenylamino)phosphonium bromide
tetrakis(di-m-tolylamino)phosphonium bromide tetrakis(dibenzylamino)phosphonium bromide
tetrakis(dicyclohexylamino)phosphonium bromide
tetrakis(dioctylamino)phosphonium bromide
tetrakis(didecylamino)phosphonium bromide
tetrakis(diethylamino)phosphonium chloride.

At present, the most preferred compound is tetrakis (diethylamino)phosphonium bromide. For a method for the preparation of such compounds, see Koidan, Marchenko, Kudryavtsev, and Pinchuk, *Zh. Obshch. Khim.*, 1982, 52, 2001, an English language translation of which is available from Plenum Publishing Corporation.

The tetra(dihydrocarbylamino)phosphonium halide catalysts are effective when utilized as the only catalyst component charged directly or indirectly (i.e., after admixture with one or more other components being charged to the reaction system. However the tetra(dihydrocarbylamino) phosphonium halide catalysts can be used in combination with one or more other types of catalysts, provided of course that the benefits provided by the tetra(dihydrocarbylamino) phosphonium halide catalyst are not materially affected adversely by the other catalyst component(s) selected for use. The tetra(dihydrocarbylamino)phosphonium halide catalysts are used in catalytically effective amounts, which typically fall in the range of about 0.01 to about 1 mole per mole of perhalobenzenes in the reaction mixture. Preferred catalytically effective amounts fall in the range of about 0.05 to about 0.3 mole per mole of perhalobenzenes in the reaction mixture.

If the reaction is performed at temperatures above about 300° C., the phosphonium catalyst in the form charged to the reaction mixture can be a tetraarylphosphonium halide, such as tetraphenylphosphonium fluoride, tetraphenylphosphonium chloride, tetraphenylphosphonium bromide, tetraphenylphosphonium iodide, and their higher aryl analogs where one or more of the aryl groups is tolyl, xylyl, mesityl, ethylphenyl, diethylphenyl, 1-naphthyl, 2-naphthyl, 1-tetrahydronaphthyl, 2-tetrahydronaphthyl, biphenylyl, etc.

As noted above, when the reaction is conducted in bulk—i.e., when no ancillary solvent or diluent is used—the reaction is performed at one or more temperatures above the melting point of hexabromobenzene, and preferably in the range of about 310° to about 370° C. The reaction mixture should be agitated to ensure intimate contact among the components in the reaction mixture. Thus the reaction can be performed, for example, in a rocking autoclave or in an autoclave equipped with mechanical stirring means.

Preferably, the reaction is performed using an ancillary solvent or diluent. This enables the reaction to be performed at lower temperatures and in general reduces utility requirements and consumption. Thus when performing the reaction in an ancillary aprotic solvent or diluent, the reaction temperature is, or the reaction temperatures are, typically in the range of about 170° to about 240° C., and the reaction slurry is maintained under pressure conditions which keep the solvent(s) or diluent(s) in the liquid state. Again it is desirable to provide sufficient agitation to ensure intimate contact among the components in the reaction slurry. Suitable aprotic solvents include sulfolane (tetramethylene sulfone), N,N-dimethylformamide, N,N-dimethylacetamide, dimethylsulfone, dimethylsulfoxide, triglyme (triethylene glycol dimethyl ether), N-methyl pyrrolidinone, benzonitrile, and the like.

To enhance its reactivity, the sodium fluoride should be in finely-divided or powdery anhydrous form. One convenient way of ensuring that the sodium fluoride is suitably anhydrous is to form a slurry of powdery sodium fluoride salt in a suitable volatile hydrocarbon such as benzene that forms an azeotrope with water, and heat the mixture to dryness, while of course suitably handling and disposing of the vapors. A particularly useful form of sodium fluoride for use in the process is may be produced by applying to NaF the procedure described by T. P. Smyth, A. Carey and B. K. Hodnett in *Tetrahedron*, Volume 51, No. 22, pp. 6363–6376 (1995). In brief, their described procedure involves recrystallizing KF from a methanol solution by slow evaporation of the solvent, followed by drying at 100° C. Another useful form of sodium fluoride is NaF dispersed on $CaF_2$. See in this connection, J. H. Clark, A. J. Hyde and D. K. Smith, *J. Chem. Soc. Chem. Commun*, 1986, 791. Other activated forms of NaF such as spray dried NaF (see N. Ishikawa, et al. *Chem. Letts*, 1981, 761), and freeze dried NaF (see Y. Kimura, et al. *Tetrahedron Letters*, 1989, 1271) can be used. When the reaction is performed in an aprotic solvent or diluent, at least one crown ether or crypt compound can be used in forming and/or can be added to the reaction slurry. These compounds, sometimes referred to as "cage compounds" can prove helpful in further enhancing the reactivity of the sodium fluoride. For a full description of the crown ethers and the crypt compounds, see U.S. Pat. No. 4,174,349 to Evans, et al. and the references cited therein relating to these materials, namely U.S. Pat. No. 3,687,978; J. J. Christensen, et al., *Chem. Rev.*, 1974, 74, 351; J. S. Bradshaw, et al., *Heterocycl. Chem.*, 1974, 11, 649; C. J. Pedersen, et al., *Angew. Chem. Int. Ed. Engl.*, 1972, 11, 16; the Technical Bulletin of PCR Incorporated entitled KRYPTOFIX; and *J. Org. Chem*, 1977, Vol 42, No. 10, 2A. The crown ether or crypt compound is used in a co-catalytically effective amount, which typically is in the range of about 0.01 to about 1 mole per mole of hexabromobenzene charged to the reaction mixture.

In another embodiment, (i) at least one polyvalent inorganic fluoride of boron, aluminum, tin, phosphorus, titanium, zirconium, hafnium, or silicon, or (ii) at least one a double salt of the polyvalent inorganic fluoride and alkali metal fluoride, or (iii) a combination of (i) and (ii), is also used in forming and/or is added to the reaction mixture in addition to the sodium fluoride, with the proviso that the inorganic fluoride of (i), (ii) and (iii) is in a stable valency state so that (i), (ii) and (iii), as the case may be, has no oxidizing properties. U.S. Pat. No. 3,453,337 to Bennett, et al., reports that in the uncatalyzed reaction between hexachlorobenzene and KF or NaF, the inclusion of compounds of the types (i), (ii) and (iii) above provides enhanced product yields using milder reaction conditions and shorter reaction times. In accordance with this embodiment of the invention, similar advantages may be achieved in the present phosphonium-catalyzed reactions. Examples of suitable polyvalent compounds include $LiBF_4$, $NaBF_4$, $KBF_4$, $K_2SnF_6$, $KPF_6$, $K_2SiF_6$, $Na_2TiF_6$, $K_2TiF_6$, $Na_2ZrF_6$, $K_2ZrF_6$, $Na_2HfF_6$, $K_2HfF_6$, among others. Such compounds can be used in co-catalytically effective amounts of up to 50% or more of the weight of the sodium fluoride charged to the reaction mixture. Typically the amount will fall in the range of about 2 to about 25 % of the weight of sodium fluoride used.

The conjoint use of (a) one or more compounds (i), (ii) and (iii) of the types described in the immediately preceding paragraph together with (b) one or more crown ethers and/or crypt compounds is also within the scope of this invention.

The following examples illustrate preferred procedures for conducting the process of this invention. All parts or percentages given in these examples are by weight. It is to be clearly understood that these examples are for the purposes of illustrating current best modes contemplated for carrying out the operations. They are not intended to limit, and should not be construed as limiting, the invention to the specific details set forth therein.

EXAMPLE 1

A mixture of 552 parts of hexabromobenzene, 294 parts of anhydrous, ball-milled or spray-dried sodium fluoride powder, and 80 parts of tetrakis(diethylamino)phosphonium bromide is heated with stirring at 500° C. for 8 hours in a sealed reactor. Perhalobenzenes are formed having at least two fluorine atoms in the molecule with the remainder, if not fluorine atoms, being bromine atoms. These perhalobenzenes are recovered by fractional distillation.

EXAMPLE 2

A mixture of 552 parts of hexabromobenzene, 294 parts of anhydrous, ball-milled sodium fluoride powder, 80 parts of tetrakis(diethylamino)phosphonium bromide, and 80 parts of potassium fluoborate is heated with stirring at 500° C. for 8 hours. Formed are perhalobenzenes having at least two fluorine atoms in the molecule, with the remainder, if not fluorine atoms, being bromine atoms.

EXAMPLE 3

To a reactor equipped with a reflux condenser with a return line for returning condensate to a location below the surface of the liquid phase of a slurry in the reactor, are charged 552 parts of hexabromobenzene, 294 parts of anhydrous, spray-dried or ball-milled sodium fluoride powder, 80 parts of tetrakis(diethylamino)phosphonium bromide and 1500 parts of sulfolane. The mixture is heated at 200° C. with stirring for 3 hours. Perhalobenzenes having at least two fluorine atoms in the molecule are formed. The remainder of the halo atoms, if other than fluorine atoms, are bromine atoms. The perhalobenzenes are recovered by filtering and fractionally distilling the reaction product mixture.

EXAMPLE 4

The procedure of Example 3 is repeated in the same manner except that 80 parts of 18-crown-6 ether is also included in the initial reaction mixture.

EXAMPLE 5

The procedure of Example 3 is repeated in the same manner except that 80 parts of crypt 222 is also included in the initial reaction mixture.

EXAMPLE 6

The procedure of Example 3 is repeated in the same manner except that the following components make up the initial charge to the reactor: (a) 552 parts of hexabromobenzene, (b) 500 parts of a mixture of pentabromofluorobenzene, tetrabromodifluorobenzene, tribromotrifluorobenzene, and dibromotetrafluorobenzene (such as recovered from the reaction mixture of a prior reaction), (c) 450 parts of activated anhydrous sodium fluoride powder (applying the method of T. P. Smyth, A. Carey and B. K. Hodnett, (loc. cit.) to NaF, (d) 150 parts of tetrakis(diethylamino)phosphonium bromide and (e) 1000 parts of sulfolane.

EXAMPLE 7

The procedure of Example 6 is repeated in the same manner except that 150 parts of 18-crown-6 ether is also included in the initial reaction mixture.

EXAMPLE 8

The procedure of Example 7 is repeated in the same manner except that 1000 parts of triglyme is used as the solvent/diluent in lieu of the sulfolane.

It is to be understood that the reactants and components referred to by chemical name or formula anywhere in the specification or claims hereof, whether referred to in the singular or plural, are identified as they exist prior to coming into contact with another substance referred to by chemical name or chemical type (e.g., another reactant, a solvent, or etc.). It matters not what preliminary chemical changes, transformations and/or reactions, if any, take place in the resulting mixture or solution or reaction medium as such changes, transformations and/or reactions are the natural result of bringing the specified reactants and/or components together under the conditions called for pursuant to this disclosure. Thus the reactants and components are identified as ingredients to be brought together in connection with performing a desired chemical reaction or in forming a mixture to be used in conducting a desired reaction. Accordingly, even though the claims hereinafter may refer to substances, components and/or ingredients in the present tense ("comprises", "is", etc.), the reference is to the substance, component or ingredient as it existed at the time just before it was first contacted, blended or mixed with one or more other substances, components and/or ingredients in accordance with the present disclosure. The fact that the substance, component or ingredient may have lost its original identity through a chemical reaction or transformation during the course of such contacting, blending or mixing operations is thus wholly immaterial for an accurate understanding and appreciation of this disclosure and the claims thereof.

Each and every patent or other publication referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

What is claimed is:

1. A process which comprises heating an anhydrous mixture containing a liquid phase and a solids phase formed from components comprising finely-divided sodium fluoride, hexabromobenzene, and an aminophosphonium catalyst, and a liquid aprotic solvent/diluent, at a temperature in the range of about 170° to about 240° C. and under pressure conditions which keep the solvent/diluent in the liquid state, and for a time at which sodium bromide and at least one hexahalobenzene containing at least two fluorine atoms are produced, said liquid aprotic solvent/diluent being present in said mixture in an amount at least sufficient to maintain said liquid phase.

2. A process according to claim 1 wherein at least one hexahalobenzene containing one to four fluorine atoms with the balance being bromine atoms, is included in said mixture.

3. A process according to claim 1 wherein at least one hexahalobenzene containing three to four fluorine atoms with the balance being bromine atoms, is included in said mixture.

4. A process according to claim 1 wherein said aminophosphonium catalyst is a tetra(dihydrocarbylamino) phosphonium halide.

5. A process according to claim 4 wherein said liquid aprotic solvent/diluent is sulfolane and said tetra(dihydrocarbylamino)phosphonium halide is a tetra(dialkylamino)phosphonium bromide.

6. A process according to claim 4 wherein at least one crown ether is also used in forming said mixture.

7. A process according to claim 4 wherein at least one crypt compound is also used in forming said mixture.

8. A process which comprises (a) brominating benzene with bromine in the presence of a Lewis acid catalyst to form hexabromobenzene; (b) forming an anhydrous mixture containing a liquid phase and a solids phase from components comprising at least a portion of said hexabromobenzene, finely-divided sodium fluoride, and an aminophosphonium catalyst, and a liquid aprotic solvent/diluent; and (c) heating said mixture at a temperature in the range of about 170° to about 240° C. and under pressure conditions which keep the solvent/diluent in the liquid state, and for a time at which sodium bromide and at least one hexahalobenzene containing at least two fluorine atoms are produced, said liquid aprotic solvent/diluent being present in said mixture in an amount at least sufficient to maintain said liquid phase.

9. A process according to claim 8 wherein excess bromine is used in (a), and said excess of bromine is also used as a component in (b) to form said mixture.

10. A process according to claim 8 wherein at least one hexahalobenzene containing one to four fluorine atoms with the balance being bromine atoms, is included in said mixture of (b).

11. A process according to claim 8 wherein at least one hexahalobenzene containing three to four fluorine atoms with the balance being bromine atoms, is included in said mixture of (b).

12. A process according to claim 8 wherein said aminophosphonium catalyst is a tetra(dihydrocarbylamino)phosphonium halide.

13. A process according to claim 12 wherein said liquid aprotic solvent/diluent is sulfolane and said tetra(dihydrocarbylamino)phosphonium halide is a tetra(dialkylamino)phosphonium bromide.

14. A process according to claim 12 wherein at least one crown ether is also used in forming said mixture.

15. A process according to claim 12 wherein at least one crypt compound is also used in forming said mixture.

* * * * *